United States Patent [19]

Koehler et al.

[11] Patent Number: 5,254,738

[45] Date of Patent: * Oct. 19, 1993

[54] PREPARATION OF 1,4-ALKYLENEDIAMINES

[75] Inventors: Ulrich Koehler, Heidelberg; Hardo Siegel, Speyer; Matthias Irgang, Heidelberg, all of Fed. Rep. of Germany

[73] Assignee: BASF Aktiengesellschaft, Lufwigshafen, Fed. Rep. of Germany

[*] Notice: The portion of the term of this patent subsequent to Jul. 21, 2009 has been disclaimed.

[21] Appl. No.: 657,632

[22] Filed: Feb. 19, 1991

[30] Foreign Application Priority Data

Mar. 6, 1990 [DE] Fed. Rep. of Germany ....... 4006979

[51] Int. Cl.$^5$ .................................... C07C 209/48
[52] U.S. Cl. .................... 564/491; 502/324; 502/326; 502/328
[58] Field of Search .............. 564/491, 490; 502/327, 502/341, 324

[56] References Cited

U.S. PATENT DOCUMENTS

| | | | |
|---|---|---|---|
| 2,166,183 | 0/1939 | Signaigo | 260/583 |
| 2,232,598 | 0/1941 | Farlow | 260/561 |
| 3,987,099 | 10/1976 | Hockele et al. | 260/584 R |
| 5,132,427 | 6/1992 | Kochler et al. | 546/246 |

FOREIGN PATENT DOCUMENTS

| | | |
|---|---|---|
| 682595 | 12/1966 | France . |
| 2543945 | 4/1983 | France . |
| 1143390 | 2/1969 | United Kingdom . |

Primary Examiner—Glennon H. Hollrah
Assistant Examiner—Brian M. Burn
Attorney, Agent, or Firm—John H. Shurtleff

[57] ABSTRACT

A process for the preparation of a 1,4-alkylenediamine of the general formula I

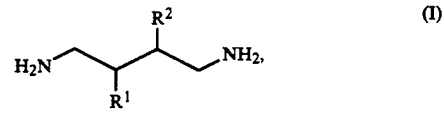

in which the substituents $R^1$ and $R^2$ are independently hydrogen, $C_1$–$C_{10}$-alkyl, phenyl or benzyl, by reacting a succinic dinitrile of the general formula II

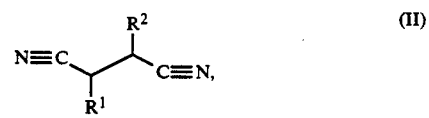

in which $R^1$ and $R^2$ have the meanings stated, with hydrogen at a temperature of from 30° to 250° C. and a pressure of from 50 to 350 bar in contact with a hydrogenation catalyst, wherein the hydrogenation catalyst used contains cobalt oxide and one or more oxides of the elements iron, nickel, manganese, chromium, molybdenum, tungsten, and phosphorus and one or more oxides of elements in the alkali metal group, alkaline earth metal group, and rare earth group of the Periodic Table, and of scandium, and/or of yttrium.

10 Claims, No Drawings

PREPARATION OF 1,4-ALKYLENEDIAMINES

The present invention relates to a novel process for the preparation of a 1,4-alkylenediamine by the reaction of a succinic dinitrile over a hydrogenation catalyst containing cobalt oxide and one or more oxides of the elements iron, nickel, manganese, chromium, molybdenum, tungsten, and phosphorus, and one or more oxides of elements in the alkali metal group, alkaline earth metal group, and rare earth group of the Periodic Table, of scandium and/or of yttrium.

U.S. Pat. No. 2,166,183 and U.S. Pat. No. 2,232,598 both describe the batch hydrogenation of succinic dinitrile in contact with activated cobalt powder (in, an autoclave), the yields being 36% and 70% respectively. JP 47/18,809 and JP 60/260,544 disclose butanediamine yields of 68% and 73%, respectively, for the batch hydrogenation of succinic dinitrile over a cobalt catalyst and in the presence of $Ca(OH)_2$ and $NH_3$, or $NH_3$ alone. Butanediamine yields of about 70% are also described in FR-A 2,248,265 with respect to the batch hydrogenation of succinic dinitrile over Raney cobalt in the presence of a tertiary amine. JP 48113,305 and JP 54/40,524 disclose yields of 97% for the batch hydrogenation of succinic dinitrile using Raney cobalt in the presence of $NH_3$ and Mn. However, this process uses 130 g of catalyst per 100 g of highly diluted substrate and is therefore not suitable for the manufacture of relatively large amounts of butanediamine on account of its poor space-time yield.

DE-A 902,616 describes a semi-continuous procedure involving the pumping of succinic dinitrile in tetrahydrofuran to a mixture of Raney cobalt, CaO, tetrahydrofuran and $NH_3$ under a hydrogen pressure of 200 bar (cf. Houben-Weyl, "Methoden der Organischen Chemie", Vol. XI, I, pp. 558 and 559). The yields are 89-93%. This process is also unsuitable for large-scale synthesis of butanediamine, because the catalyst rapidly becomes inactive.

DE-A 954,416 describes the continuous hydrogenation of succinic dinitrile over a cobalt catalyst deposited on silica extrudates and neutralized by the addition of 0.25% of phosphoric acid. The yields are- about 92%. DE-A 1,593,764-relates to continuous hydrogenation in the presence of $NH_3$ using a catalyst composed of 30% w/w of cobalt on pumice and impregnated with 10% w/w of aqueous $Na_2CO_3$ solution. The above catalysts are characterized by very rapid deactivation, however, their on-stream period being less than 3 days, as confirmed by Comparative Example 7 below. It is thus an object of the present invention to provide a process which overcomes the above drawbacks.

Accordingly, we have found a novel and improved process for the preparation of a 1,4-alkylenediamine of the general formula I

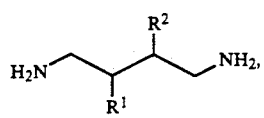

(I)

in which the substituents $R^1$ and $R^2$ are independently hydrogen, $C_1$–$C_{10}$-alkyl, phenyl or benzyl, by reacting a succinic dinitrile of the general formula II

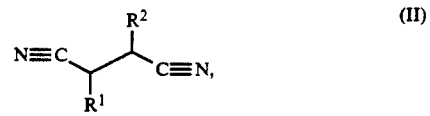

(II)

in which $R^1$ and $R^2$ have the meanings stated, with hydrogen at a temperature of from 30° to 250° C. and a pressure of from 50 to 350 bar in contact with a hydrogenation catalyst, wherein the hydrogenation catalyst used contains cobalt oxide and one or more oxides of the elements iron, nickel, manganese, chromium, molybdenum, tungsten, and phosphorus, and one or more oxides of elements in the alkali metal group, alkaline earth metal group, and rare earth group of the Periodic Table, and of scandium and/or of yttrium.

The process of the present invention is generally carried out at a temperature of from 30° to 250° C., preferably from 50° to 170° C. and more preferably from 60° to 150° C. and under a pressure of from 50 to 350 bar, preferably from 150 to 350 bar, the catalyst used being one which contains cobalt oxide and one or more oxides, preferably one to three oxides selected from oxides of the elements iron, nickel, manganese, chromium, molybdenum, tungsten, and phosphorus, and one or more oxides, preferably from one to three oxides and more preferably one oxide selected from the oxides of elements in the alkali metal group, alkaline earth metal group, and rare earth group, and of scandium and/or of yttrium. Suitable oxides of the elements iron, nickel, manganese, chromium, molybdenum, tungsten, and phosphorus are $Fe_2O_3$, NiO, $Ni_2O_3$, $MnO_2$, $Mn_3O_4$, $MoO_3$, $CrO_3$, $Cr_2O_3$, $WO_3$, and $P_2O_5$. Suitable oxides of alkali metals or alkaline earth metals are for example $LiO_2$, $Na_2O$, $K_2O$, MgO, CaO, SrO, and BaO. Examples of suitable oxides -of- rare earths are $La2O3$, $Ce2O3$, $Gd2O3$, $Dy2O3$, $SM2O3$, $Nd2O3$, and $Er2O3$. By catalytically active material below we mean the material comprising the said metal oxide(s) excluding supporting material. The catalysts may consist of from 5% to 100% w/w of catalytically active material.

Particularly suitable catalysts are for example those in which from 20% to 95% w/w and preferably from 40% to 90% w/w of the catalytically active material consists of cobalt oxide and from 0.5% to 60% w/w and preferably from 1% to 40% w/w of the catalytically active material consists of one or more oxides of the elements iron, nickel, manganese, chromium, molybdenum, tungsten, and phosphorus, preferably one or more oxides of the metals manganese, nickel, and iron, and from 0.5% to 20% w/w of the catalytically active material consists of one or more oxides of elements in the alkali metal group, alkaline earth metal group, or rare earth group, or of scandium, or of yttrium.

The catalysts may be used in the form of solid catalysts, e.g. granules, or in the form of supported catalysts in which the inert support is, say, silicon dioxide, aluminum oxide, a zeolite, titanium dioxide, magnesium oxide, pumice, zirconium oxide, or carbon. A catalyst containing metal components in the form of their oxides will generally be activated before use by means of a hydrogen treatment in which some of the oxide will be reduced to metal.

The hydrogen employed for hydrogenation is generally used in a relatively large stoichiometric excess of from 1 to 25 times, preferably from 2 to 10 times, the stoichiometric amount required. It can be recycled to the reaction. The hydrogen used is generally commercially pure hydrogen, but additional contents of inert gas, e.g. nitrogen, have no adverse effect on the reaction rate.

It is advantageous to add ammonia in order to diminish the formation of secondary amines, e.g. pyrrolidines. The process is generally operated using a molar ratio of ammonia to succinic dinitrile of from 1:1 to 100:1, preferably from 2:1 to 20:1.

The succinic dinitrile of formula II can be used in substance or dissolved in a suitable solvent, examples of which are ethers such as cyclic ethers, e.g. tetrahydrofuran or dioxane, alcohols such as $C_1$-$C_4$-alcohols, e.g. methanol and ethanol, or other solvents conventionally used in hydrogenations, such as formamides, e.g. dimethyl formamide or N-methylpyrrolidone.

The hydrogenation may be carried out batchwise, but it is preferably operated as a continuous process involving the use of a fixed bed, e.g. in a trickle bed column or a packed bubble column. When operating batchwise, a succinic dinitrile or solution thereof is placed in a high-pressure autoclave together with the catalyst, and ammonia and hydrogen are pumped in, both in excess, and the reaction mixture is heated. On completion of the reaction, the mixture is cooled and the catalyst separated, after which the reaction mixture is fractionally distilled.

Continuous operation is effected, for example, by packing a vertical reactor with one of said catalysts and metering in, from the top, succinic dinitrile or a solution thereof, ammonia and hydrogen in the desired ratio (trickle process). The stated conditions of pressure and temperature are maintained throughout the reaction. On leaving the reactor, the reaction mixture is cooled and divided into a liquid component and a gaseous component (hydrogen). The liquid component is freed from ammonia and solvent and then purified by distillation. Ammonia, hydrogen and a portion of the crude liquid effluent can be recycled to the reactor to complete the reaction and dissipate the heat of reaction.

Using these conditions, it is possible to obtain 1,4-alkylenediamines of formula I in yields of more than 97% over on-stream periods exceeding 2 months.

1,4-Alkylenediamines are valuable intermediates. For example, 1,4-butanediamine is used as the amine component in Nylon ®-4,6.

EXAMPLES

In the following Examples, the percentages are by weight.

EXAMPLE 1

Preparation of suitable catalysts

Catalyst A (extrudates)

An aqueous solution containing cobalt nitrate, iron nitrate, and manganese nitrate and a 30% aqueous sodium bicarbonate solution are metered through separate pumps into a stirred vessel at rates adjusted to keep the pH constant at 6.5. The temperature in this precipitation vessel is kept at 50° C.

The precipitated product is pumped to a filter press and washed until free from sodium.

The filter cake is mixed with calcium hydroxide powder (10% of CaO based on total oxides) in a mixer, dried and calcined at 500° C. The product thus obtained is compressed in a kneader until it has a consistency suitable for shaping. The material is extruded, dried and recalcinated, at 650° C. The 4 mm extrudates have the following chemical composition (calculated as free from combustion weight losses):
65.2% of CoO
4.7% of $Mn_3O_4$
10.0% of CaO
20.1% of $Fe_2O_3$.

Catalyst B (extrudates)

From an aqueous solution containing cobalt nitrate, iron nitrate, nickel nitrate, and manganese nitrate there is precipitated a catalyst precursor with soda solution as described for Catalyst A, which is then dried and washed.

The filter cake is mixed with calcium hydroxide powder (10% of CaO based on total oxides) in a mixer, dried and calcined, as above, at 500° C. The product thus obtained is compressed in a kneader until it has a consistency suitable for shaping. The material is extruded, dried and recalcinated, at 650° C. The 4 mm extrudates have the following chemical composition (calculated as free from combustion weight losses):
69.2% of CoO
4.9% of $Mn_3O_4$
5.5% of NiO
10.4% of $Fe_2O_3$
10.0% of CaO.

EXAMPLE 2

Batch Hydrogenation of Methyl Succinic Dinitrile 50 g of-methyl succinic dinitrile II ($R^1$=$CH_3$, $R^2$=H), 50 g of tetrahydrofuran and 10 g of Catalyst A (in a wire mesh basket) are placed in an autoclave. This is purged with nitrogen, and 120 ml of ammonia are added. The temperature is raised to 100° C. and hydrogen is pumped in to create an internal pressure of 300 bar with replenishment of hydrogen each hour. When hydrogen absorption has ceased, the reaction mixture is cooled, depressurized and filtered. The filtrate is concentrated and distilled to give 52.0 g (95.8%) of methyl butanediamine I ($R^1$=$CH_3$, $R^2$=H).

EXAMPLE 3

Batch Hydrogenation of Methyl Succinic Dinitrile

Example 2 is repeated except that a catalyst is used which has the following composition: 65.3% of CoO, 5.2% of MnO, 10.3% of $Fe_2O_3$, and 19.2% of $La_2O_3$. There are obtained 53.9 g (99.4%) of methyl butanediamine I.

EXAMPLE 4

Batch Hydrogenation of Succinic Dinitrile

Example 3 is repeated except that 50 g of succinic dinitrile II ($R^1$=H, $R^2$=H) are used. There are obtained 54.2 g (98.5%) of butanediamine I ($R^1$=H, $R^2$=H).

EXAMPLE 5

Continuous Hydrogenation of Succinic Dinitrile

A trickle-bed reactor having a length of 3 m and an internal diameter of 16 mm is packed with Catalyst B (cf. Example 1). A 50% solution of succinic dinitrile II ($R^1$=H, $R^2$=H) in tetrahydrofuran is fed to the top of the reactor. The feed of succinic dinitrile solution is maintained at 250 ml/h, ammonia is added at the rates given below and the hydrogen pressure is kept at 300 bar while liquid is recycled at a rate of 9 l/h. Three tests are carried out at different temperatures. The effluents are concentrated and distilled. The products are obtained in the proportions listed in the Table below:

| Temp. [°C.] | Feed of NH₃ [ml/h] | Butanediamine [%] | Pyrrolidine [%] | Residues [%] |
|---|---|---|---|---|
| 80 | 400 | 97.3 | <0.5 | 1.2 |
| 100 | 400 | 98.5 | <0.5 | 0.8 |
| 150 | 200 | 90.1 | 5.3 | 2.7 |

EXAMPLE 6

Continuous Hydrogenation of Succinic Dinitrile

A reactor suitable for use as a packed bubble column and having a length of 2 m and an internal diameter of 41 mm is packed with catalyst extrudates having a length of 7 mm and a diameter of 4 mm. The catalyst contains the following active ingredients: 70.3% of CoO, 10.5% of NiO, 5.2% of MnO, and 14.0% of $Na_2O$. A 40% solution of succinic dinitrile II ($R^1=H$, $R^2=H$) in methanol is fed to the bottom of the reactor. Hydrogen and ammonia are also introduced at the bottom. The feed of methanolic dinitrile solution is 700 ml/h and that of the ammonia is 500 ml/h, while the hydrogen pressure is maintained at 300 bar and the flow of recycled liquid is adjusted to 40 l/h. The effluent is worked up as described in Example 5. Using a temperature of 80° C., the following fractions are obtained: 98.7% of butanediamine, <0.5% of pyrrolidine, and 0.8% of residues.

EXAMPLE 7

Continuous Hydrogenation of Succinic Dinitrile (Comparative Test)

In three different tests, the trickle-bed reactor of Example 5 is packed with the catalyst described in DE-A 954,416, Example 3, that described in DE-A 1,593,764, Example 1, and Catalyst B of Example 1 above, respectively. In each test, a 50% solution of succinic dinitrile ($R^1=H$, $R^2=H$) in tetrahydrofuran is fed at a rate of 150 ml/h, ammonia is introduced at a rate of 240 ml/h, and the recycle rate is 9 l/h, while the temperature is kept at 100° C. and the hydrogen pressure at 300 bar. The products are worked up as described in Example 5 and give the following yields of butanediamine with respect to time:

| | Yield of butanediamine [%] after | | | |
|---|---|---|---|---|
| | 24 h | 48 h | 1 week | 4 weeks |
| DE-A 954,416, Example 1 | 78.2 | 65.3 | <50 | — |
| DE-A 1,593,764, Example 1 | 75.7 | <50 | — | — |
| Catalyst B of Example 1 | 98.1 | 98.9 | 97.9 | 98.2 |

Catalyst B could be used for an on-stream period of more than 2 months, whereas the other two catalysts made it necessary to stop after only a short on-stream period due to clogging.

We claim:

1. A process for the preparation of a 1,4-alkylenediamine of the formula

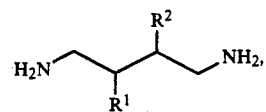

in which the substituents $R^1$ and $R^2$ are independently hydrogen, $C_1$-$C_{10}$-alkyl, phenyl or benzyl, which comprises reacting a succinic dinitrile of the formula

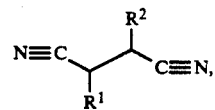

in which $R^1$ and $R^2$ have the meanings stated, with hydrogen at a temperature of from 30° to 250° C. and a pressure of from 50 to 350 bar in contact with a hydrogenation catalyst, wherein the hydrogenation catalyst used contains cobalt oxide and one or more oxides of the elements iron, nickel, manganese, chromium, molybdenum, tungsten, and phosphorus and one or more oxides of elements in the alkali metal group, alkaline earth metal group, and rare earth group of the Periodic Table, and of scandium, and/or of yttrium.

2. A process as claimed in claim 1, wherein the hydrogenation catalyst contains, as catalytically active material, from 20% to 95% w/w of cobalt oxide, from 0.5% to 60% w/w of one or more oxides of the metals manganese, nickel, iron, chromium, molybdenum, tungsten, or phosphorus and from 0.5% to 20% w/w of one or more oxides of elements in the alkali metal group, alkaline earth metal group, and rare earth group, of scandium, and/or of yttrium.

3. A process as claimed in claim 1, wherein the active material of said hydrogenation catalyst used in the reaction consists essentially of:
   (a) at least 40% w/w of cobalt oxide;
   (b) at least 1% w/w of an oxide of at least one of the elements iron, nickel, manganese, chromium, molybdenum, tungsten and phosphorus; and
   (c) at least 0.5% w/w of an oxide of at least one of the elements selected from the group consisting of alkali metals, alkaline earth metals, rare earth metals, scandium and yttrium.

4. A process as claimed in claim 3, wherein the proportions of the three essential components of the catalytically active material are from 40 to 90% w/w of (a), from 1 to 40% w/w of (b) and from 0.5 to 20% w/w of (c).

5. A process as claimed in claim 4, wherein component (b) is an oxide of at least one of the metals, iron, nickel and manganese.

6. A process as claimed in claim 3, wherein ammonia is added to the reaction in a molar ratio of ammonia to succinic dinitrile of from 1:1 to 100:1.

7. A process as claimed in claim 3, wherein ammonia is added to the reaction in a molar ratio of ammonia to succinic dinitrile of from 2:1 to 20:1.

8. A process as claimed in claim 3, wherein the reaction is carried out continuously.

9. A process as claimed in claim 1, wherein the reaction is carried out at a temperature of from 50° to 170° C. and a pressure of from 150 to 350 bar.

10. A process as claimed in claim 1, wherein the catalyst consisting essentially of said oxides as the catalytically active material is carried on an inert support in an amount of at least 5% by weight, based on the total weight of the oxides and the inert support.

* * * * *